United States Patent
Li et al.

(10) Patent No.: US 10,421,151 B2
(45) Date of Patent: Sep. 24, 2019

(54) LASER NOISE ELIMINATION IN TRANSMISSION THERMOMETRY

(71) Applicants: Jiping Li, Palo Alto, CA (US); Aaron Muir Hunter, Santa Cruz, CA (US); Thomas Haw, Portland, OR (US)

(72) Inventors: Jiping Li, Palo Alto, CA (US); Aaron Muir Hunter, Santa Cruz, CA (US); Thomas Haw, Portland, OR (US)

(73) Assignee: Applied Materials, Inc., Santa Clara, CA (US)

(*) Notice: Subject to any disclaimer, the term of this patent is extended or adjusted under 35 U.S.C. 154(b) by 1265 days.

(21) Appl. No.: 13/789,982

(22) Filed: Mar. 8, 2013

(65) Prior Publication Data

US 2013/0264316 A1 Oct. 10, 2013

Related U.S. Application Data

(60) Provisional application No. 61/618,153, filed on Mar. 30, 2012.

(51) Int. Cl.
*B23K 26/00* (2014.01)
*G01N 21/59* (2006.01)
(Continued)

(52) U.S. Cl.
CPC .......... *B23K 26/00* (2013.01); *G01J 1/0459* (2013.01); *G01J 5/0007* (2013.01); *G01J 5/02* (2013.01);
(Continued)

(58) Field of Classification Search
CPC .... B23K 26/00; B23K 26/0639; G01N 21/59; G01N 21/1702; G01J 5/02; G01J 5/58;
(Continued)

(56) References Cited

U.S. PATENT DOCUMENTS 5,035,144 A * 7/1991 Aussel ................ G01N 29/075
                                                    73/602
6,128,081 A * 10/2000 White ................. G01B 11/0666
                                                    356/432
(Continued)

FOREIGN PATENT DOCUMENTS

| JP | H10-111186 A | 4/1998 |
|----|--------------|--------|
| TW | 201003727 A  | 1/2010 |
| TW | 201011839 A  | 3/2010 |

OTHER PUBLICATIONS

International Search Report and Written Opinion dated Jul. 26, 2013, in International Application PCT/US2013/029973.
(Continued)

*Primary Examiner* — Dana Ross
*Assistant Examiner* — Joseph W Iskra
(74) *Attorney, Agent, or Firm* — Patterson + Sheridan, LLP

(57) ABSTRACT

Apparatus and methods for measuring the temperature of a substrate are disclosed. The apparatus includes a source of temperature-indicating radiation, a detector for the temperature-indicating radiation, and a decorrelator disposed in an optical path between the source of temperature-indicating radiation and the detector for the temperature-indicating radiation. The decorrelator may be a broadband amplifier and/or a mode scrambler. A broadband amplifier may be a broadband laser, Bragg grating, a fiber Bragg grating, a Raman amplifier, a Brillouin amplifier, or combinations thereof. The decorrelator is selected to emit radiation that is transmitted, at least in part, by the substrate being monitored. The source is matched to the decorrelator such that the emission spectrum of the source is within the gain bandwidth of the decorrelator, if the decorrelator is a gain-driven device.

17 Claims, 4 Drawing Sheets

(51) Int. Cl.
*G01J 5/02* (2006.01)
*G01J 5/08* (2006.01)
*G01J 1/04* (2006.01)
*G01J 5/00* (2006.01)
*G01J 5/06* (2006.01)
*G01J 5/58* (2006.01)

(52) U.S. Cl.
CPC ............... *G01J 5/06* (2013.01); *G01J 5/0896* (2013.01); *G01J 5/58* (2013.01); *G01N 21/59* (2013.01)

(58) Field of Classification Search
CPC .......... G01J 5/0007; G01J 5/06; G01J 5/0896; G01J 1/0459; G01B 11/0675
USPC ................ 219/121.6; 374/121; 356/432, 503
See application file for complete search history.

(56) References Cited

U.S. PATENT DOCUMENTS

| | | | |
|---|---|---|---|
| 7,112,763 B2 | 9/2006 | Hunter et al. | |
| 7,543,981 B2* | 6/2009 | Timans | G01K 11/125 250/338.1 |
| 7,628,531 B2* | 12/2009 | Lee | G01K 11/32 374/1 |
| 8,254,767 B2 | 8/2012 | Hunter et al. | |
| 2003/0236642 A1* | 12/2003 | Timans | G01J 5/0003 702/99 |
| 2004/0032646 A1* | 2/2004 | Koren | H01S 5/5018 359/344 |
| 2007/0223556 A1 | 9/2007 | Lee et al. | |
| 2007/0268477 A1* | 11/2007 | Dams | G01J 5/02 356/43 |
| 2009/0122827 A1* | 5/2009 | Schanz | G01J 5/0003 374/2 |
| 2009/0316749 A1 | 12/2009 | Davis | |
| 2009/0321415 A1* | 12/2009 | Zhang | H05B 1/0294 219/528 |
| 2010/0003020 A1 | 1/2010 | Ranish et al. | |
| 2010/0267173 A1* | 10/2010 | Moffatt | B23K 26/0604 438/16 |

OTHER PUBLICATIONS

Taiwan Office Action issued in Application No. 107108015 dated Jan. 3, 2019.
Chinese Office Action for Application No. 201380014791.7 dated May 17, 2017.
Taiwan Office Action for Application No. 102109887 dated May 26, 2017.

* cited by examiner

LASER NOISE ELIMINATION IN TRANSMISSION THERMOMETRY

CROSS-REFERENCE TO RELATED APPLICATIONS

This application claims benefit of U.S. provisional patent application Ser. No. 61/618,153, filed Mar. 30, 2012, which is herein incorporated by reference.

FIELD

Embodiments described herein relate to apparatus and methods of annealing substrates. More specifically, apparatus and methods described herein relate to temperature measurement by radiation transmission.

BACKGROUND

Transmission pyrometry is a common mode of detecting the thermal state of a substrate. Thermal processing chambers commonly expose a substrate to intense, non-coherent or coherent radiation to raise the temperature of the substrate, either of the whole substrate or a part or surface area of the substrate. The radiation used to heat the substrate creates a strong background radiation environment in the chamber.

High power radiation is used to detect the thermal state of the substrate because it can be differentiated from the background radiation in the chamber. Lasers are typically used because they offer high power, and because they afford the opportunity to select a particular wavelength best suited to the substrate. Lasers produce coherent radiation that, when transmitted through a substrate, can indicate a thermal state of the substrate, which may be registered as a temperature. The transmitted radiation may be detected by a pyrometer and compared to the incident radiation, and the transmission is correlated to the substrate thermal state.

Radiation generated by lasers typically has a very narrow spectral width, and the precise wavelength of the radiation varies detectably as the laser operates. Temperature of the lasing medium affects the wavelength emitted by the laser, but even temperature-controlled lasers exhibit noise due to, for example, mode-hopping. As this varying radiation impacts a substrate, some of the radiation reflects between the opposite surfaces of the substrate, producing an interference effect. As the wavelength of the laser light varies, the combined effect of the laser light and the interference produces a great deal of noise in the transmitted light that reduces the ability of the pyrometer to detect the thermal state of the substrate with accuracy.

Combined with the noise inherent in the laser radiation is the effect of temperature on the substrate. As the substrate temperature changes, its refractive index may change, and its thickness may change, altering the interference patterns observed. These combined noise sources greatly reduce the ability to correlate transmitted radiation to thermal state, because the intensity of the transmitted radiation is modulated by varying interference effects.

Thus, there is a need for apparatus and methods of low-noise transmission measurement.

SUMMARY

Apparatus and methods for measuring the temperature of a substrate are disclosed. The apparatus includes a source of temperature-indicating radiation, a detector for the temperature-indicating radiation, and a decorrelator disposed in an optical path between the source of temperature-indicating radiation and the detector for the temperature-indicating radiation. The decorrelator may be a broadband amplifier and/or a mode scrambler. A broadband amplifier may be a broadband laser, Bragg grating, a fiber Bragg grating, a Raman amplifier, a Brillouin amplifier, or combinations thereof. The decorrelator is selected to emit radiation that is transmitted, at least in part, by the substrate being monitored. The source is matched to the decorrelator such that the emission spectrum of the source is within the gain bandwidth of the decorrelator, if the decorrelator is a gain-driven device.

A thermal processing chamber may have a transmission thermal analyzer as described herein. The chamber has a substrate support in an enclosure, a heat source adjacent to the substrate support for heating a substrate disposed on the substrate support, and a transmission assembly including a source of coherent radiation, a decorrelator, and a detector positioned such that radiation emitted by the decorrelator passes the substrate support on its way to the detector. The decorrelator may increase the number of modes in the radiation, or may broaden the spectrum of the radiation to prevent a noisy signal from reaching the detector.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
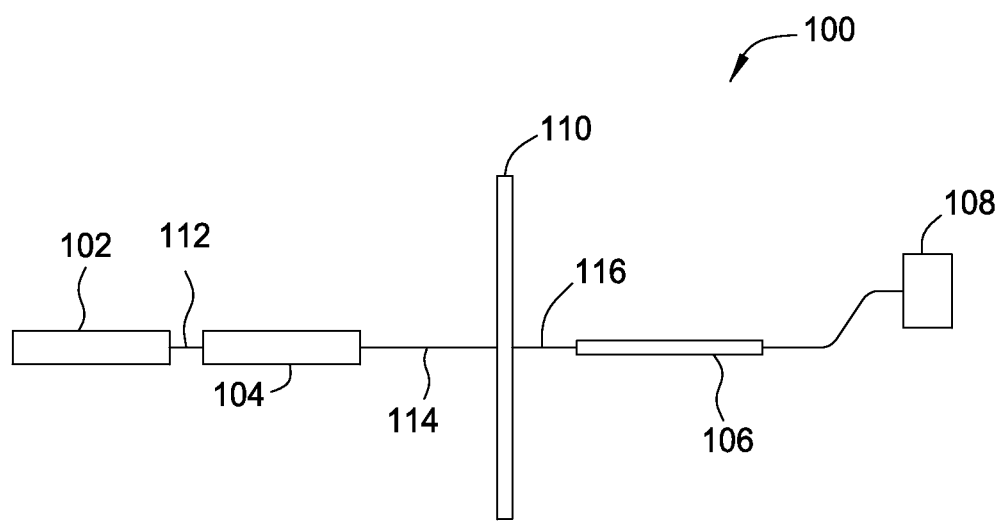
FIG. 1 is a schematic view of a temperature measurement apparatus according to one embodiment.

FIG. 1 is a schematic view of an apparatus 100 for determining the thermal state of a substrate 110, according to one embodiment. The apparatus 100 comprises a source 102 of coherent thermal radiation 112, a decorrelator 104 that converts the coherent thermal radiation 112 into a decorrelated thermal radiation 114, a detector 106 that detects transmitted radiation 116 that has been transmitted through the substrate 110, and a data processor 108, such as a computer, for transforming the signal from the detector 106 into an indication of the thermal state of the substrate 110.

The source 102 may be a laser, such as a laser diode, or another superluminescent source, such as a light-emitting diode (LED). To accurately detect the thermal state of a substrate, the source 102 is generally a source that emits a narrow spectrum of radiation, so that the absorption of that radiation by the substrate can be accurately determined. In most embodiments, the source 102 is a laser diode. Laser diodes emitting at wavelengths of at least about 950 nm, for example 980 nm, 1024 nm, or other such wavelengths, are frequently used for detecting the thermal state of substrates that are mostly made of silicon.

The decorrelator 104 broadens the spectrum of the radiation received from the source 102 and/or reduces coherency of the received radiation. The broadened spectrum and/or decorrelated radiation reduces interference of light reflected through the substrate, reducing the noise in the transmitted radiation. The detector 106 therefore indicates the thermal state of the substrate 110 with more accuracy.

The decorrelator 104 may be a broadband amplifier in some embodiments. A broadband amplifier is generally an amplifier of radiation that accepts an input radiation and amplifies it across a relatively broad spectrum. In one embodiment, such an amplifier is a lasing medium engineered to have geometry that supports a broad range of resonant frequencies. A crystal lasing medium with reflective inclusions that produce a multi-resonant cavity is one example. In other embodiments, radiation is amplified through optical nonlinearities, resulting in a spectral broadening. Examples of broadband amplifiers that may be used include a broadband laser, a Bragg grating, a fiber Bragg grating, a fiber laser, an etalon, a Raman amplifier, and a Brillouin amplifier. The decorrelator may also be a mode scrambler.

In embodiments featuring a gain-driven broadband amplifier, the gain spectrum of the broadband amplifier typically includes the emission spectrum of the source 102, such that the radiation emitted by the source 102 is spectrally broadened by the broadband amplifier. The broadband amplifier will typically have a spectral bandwidth, or emission bandwidth, between about 50 THz and about 1,000 THz, such as between about 300 THz and about 700 THz, for example about 500 THz. If the source 102 has a narrow bandwidth, for example a single-frequency laser, the emission of the source 102 may be selected within the gain spectrum of the broadband amplifier, or the broadband amplifier may be matched to the source 102.

The radiation emitted from the decorrelator 104 is typically selected to have a wavelength at least partially transmitted by the substrate 110. In cases where the decorrelator 104 has no spectral effect on the radiation, the radiation emerging from the decorrelator 104 will have substantially the same wavelength and spectrum as the radiation received from the source 102. In cases where the decorrelator 104 changes the spectral distribution of the radiation, as with most broadband amplifiers, the decorrelator and the source may be matched such that the decorrelator has a gain bandwidth that covers the emission spectrum of the source, while the decorrelator emission spectrum contains one or more wavelengths transmitted by the substrate.

The radiation emitted by the source will typically have a first primary wavelength, such as a first mode, while the radiation emitted by the decorrelator, which may be a broadband amplifier, will typically have a second primary wavelength, such as a second mode. In most cases, the difference between the first mode and the second mode, or the first primary wavelength and the second primary wavelength, is between about 5 nm and about 20 nm, such as between about 6 nm and about 10 nm, for example about 6 nm. It should be noted that the difference depends on selection of the source and decorrelator types. If the source is used as a pump for a broadband amplifier, operating for example as a broadband laser, the source has an emission spectrum within the gain spectrum of the broadband amplifier. If the broadband amplifier is a mode-dispersed broadband Nd:YAG laser emitting around 1,064 nm with $M^2$ greater than about 30 and spectral bandwidth around 560 THz, for example, the source may be a single-frequency laser emitting at 808 nm or 869 nm, near the center of the two gain bands of an Nd:YAG laser.

The detector 106 is typically a pyrometer, but may be another type of radiation detector where convenient. For example a photodiode array or CCD array may also be used. In one embodiment, a diode laser emitting a narrow bandwidth 1,030 nm radiation is used as the source, and is coupled to a fiber Bragg grating ("FBG") having an emission spectrum offset of about 6-10 nm and a spectral width of about 1.6-2.0 nm. A pyrometer detects the radiation emerging from the FBG and registers an electric current that is transformed into an indicator of the thermal state of the substrate, such as temperature, by the data processor 108.

The source 102 may be a temperature-dependent emitter. For example, laser diode generally emit radiation that has a wavelength that depends on the temperature of the lasing medium. For example, the emission wavelength of an InGaAs laser diode typically has a temperature dependence of about 0.25 nm/° C. The wavelength of the emitted radiation can therefore be tuned to a degree in some embodiments. Tuning the emitted radiation may be useful to match the emitted radiation to the properties of the decorrelator 104 for best results. In a laser diode embodiment, a thermoelectric cooler may be coupled to the lasing medium to provide a desired amount of cooling. A wavelength can be found that provides the best accuracy by monitoring noise in the signal detected by the detector 108 while adjusting the temperature of the lasing medium to find a setting that minimizes the noise in the signal.

Figure 2:
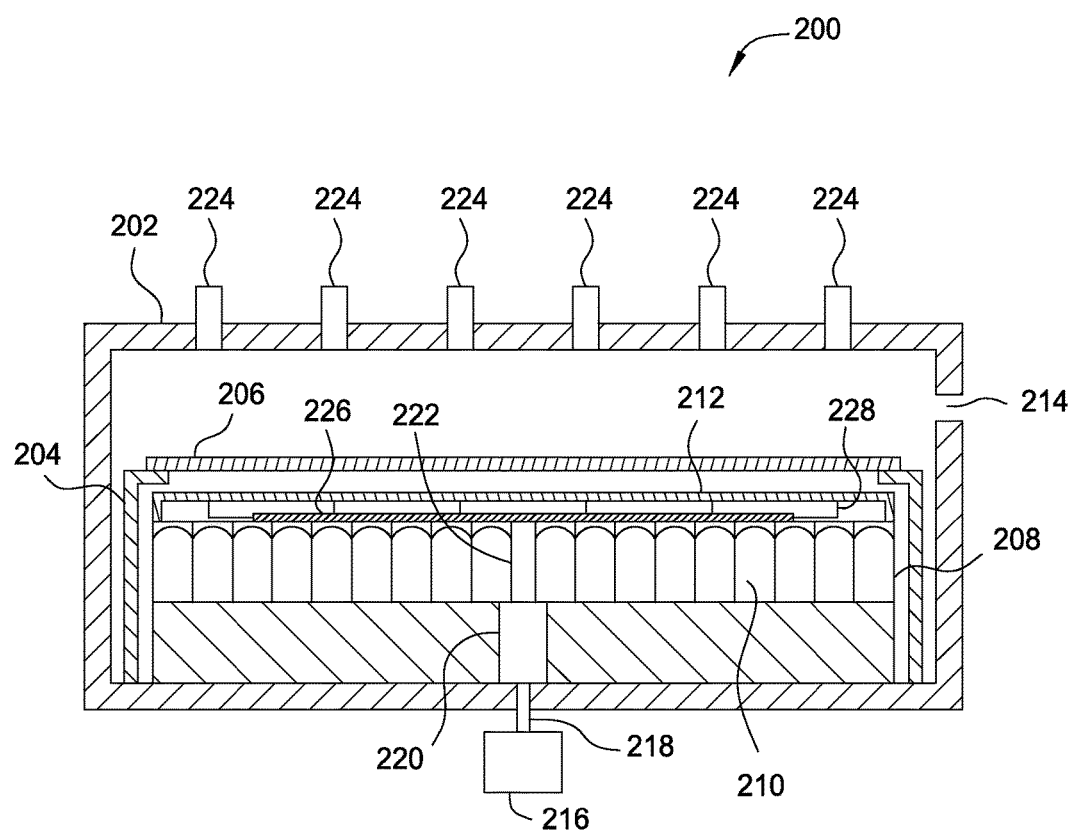
FIG. 2 is a schematic side view of a thermal processing chamber according to another embodiment.

FIG. 2 is a schematic side view of an apparatus 200 according to another embodiment. The apparatus 200 is a thermal processing chamber with a transmission thermal analysis apparatus as described above in connection with FIG. 1. A thermal processing chamber such as the VULCAN® chamber available from Applied Materials, Inc., of Santa Clara, Calif., may be used with a thermal analyzer according to any of the embodiments described in reference to FIG. 1. Other thermal processing apparatus, for example RTP chambers available from other manufacturers, may also benefit from embodiments described herein.

The apparatus 200 comprises an enclosure 202 enclosing a substrate support 204 on which a substrate 206 may be disposed. The substrate 206 enters the enclosure 202 through an opening 214 by a transportation mechanism not shown in FIG. 2. The substrate transportation mechanism may be any conventional mechanism known to the art.

A heater 208 is disposed in the enclosure 202 adjacent to a processing position of the substrate 206 such that the substrate 206 may be thermally processed by the heater 208. The heater 208 may be a bank of high intensity lamps 210, such as discharge lamps, arranged in an array to provide uniform thermal radiation to the substrate 206. A window 212, which may be a quartz window, shields the heater 208 from the processing environment of the chamber. A rotation mechanism (not shown) is typically included in the chamber.

A thermal analysis assembly comprising a source 216 of coherent thermal radiation, a decorrelator 220 optically coupled to the source 216 by a first optical conduit 218, and a detector 224 disposed such that the radiation leaving the decorrelator 220 passes the substrate support 204 on its way to the detector 224. The radiation leaving the decorrelator 220 propagated through a second optical conduit 222 disposed through the heater 208.

The source 216, decorrelator 220, and detector 224 may be any of the embodiments described above in connection with FIG. 1. The optical conduit 218 may be a fiber in some embodiments. In other embodiments, the source 216 may be directly coupled, for example physically coupled to, or contacting, the decorrelator 220. In some cases the source 216 and the decorrelator 220 may be welded, or the decorrelator 220 may be welded to the conduit 218. The detector 224 may be coupled to a data processing device as shown in FIG. 1.

In some embodiments, the detector 224 may be a plurality of individual sensors, which may be distributed at different locations to measure the thermal state of the substrate at different locations. In such an embodiments, the radiation emitted by the decorrelator 220 may be divided, for example by an optical splitter 226, which may be a fiber bundle, that directs portions of the decorrelated radiation to different locations of the substrate 206 by conduits 228 for detection by the individual sensors of the detector 224.

In one embodiment, the conduit 218 and the decorrelator 220 are optically coupled by an anti-reflective coupling. One type of anti-reflective coupling is a flat face coupling, in which a facet of the conduit 218 and an opposite facet of the decorrelator 220 are each perpendicular to the optical path, and each has an anti-reflective coating. Another type of anti-reflective coupling is a physical coupling, such as welding, where the interface between the conduit 218 and the decorrelator 220 is compositionally gradated to afford a smooth index change to minimize reflection. A third type of anti-reflective coupling is an angled polished connection, where a facet of the conduit 218 and an opposite facet of the decorrelator 220 are angled with respect to the optical path such that any reflected radiation is dissipated away from the optical path.

In operation, a method of transmission is used that reduces or eliminates noise in the detection of the thermal state of a substrate. A source of coherent radiation is positioned so as to irradiate a portion of a substrate with radiation that is transmitted at least in part through the substrate. A detector receives the transmitted radiation and produces a signal based on the transmitted radiation. The coherent radiation emitted by the source is subjected to spectral broadening and/or decorrelation using a decorrelator, which may be a broadband amplifier as described above in connection with FIGS. 1 and 2. Noise in the detected signal may be minimized by adjusting the wavelength of the coherent radiation. The wavelength of the coherent radiation may be adjusted in a tunable laser, for example by coupling a thermo-electric cooler to a laser diode. In one embodiment, temperature of the laser diode is adjusted from about 0° C. to about 50° C., such as from about 0° C. to about 40° C., for example from about 0 ° C. to about 25° C., to reduce noise in the detected signal.

The properties of the decorrelator are typically matched to the properties of the radiation source such that the radiation source provides radiation that is effectively decorrelated by the decorrelator. For example, if the decorrelator is a broadband amplifier, the emission spectrum of the radiation source is typically selected to be within a gain bandwidth of the broadband amplifier. The broadband amplifier is selected to provide broadband radiation that is transmitted, at least in part, by the substrate. It is preferred that substantially all the radiation emitted by the decorrelator is in a range that is transmitted by the substrate as a function of thermal state, for example temperature, such that the detector may correlate transmitted radiation to thermal state.

It should be noted that, although FIG. 2 depicts an apparatus wherein the source 216, conduit 218, and decorrelator 220 are inside the enclosure 202, the source 216, conduit 218, and decorrelator 220 may be located outside the enclosure in some embodiments.

Figure 3B:
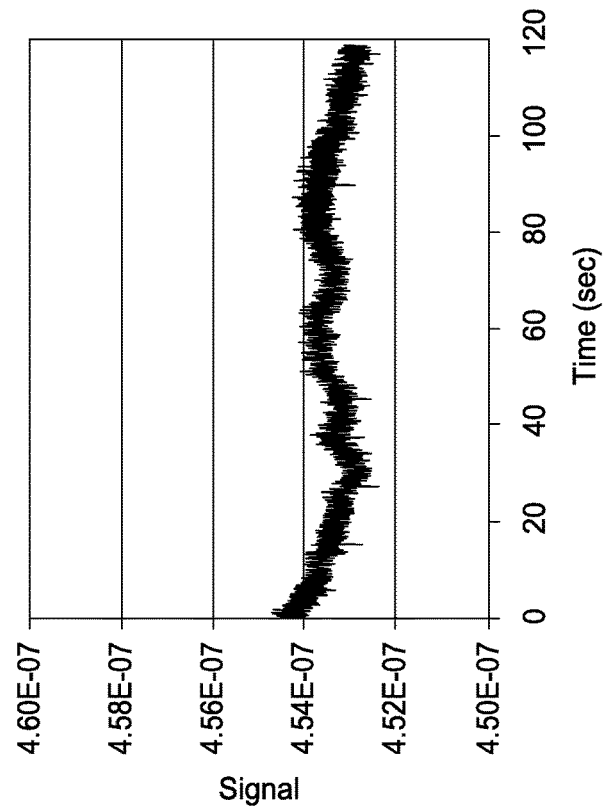
FIG. 3B is a graph showing a transmission signal of an embodiment of the invention.
Figure 3A:
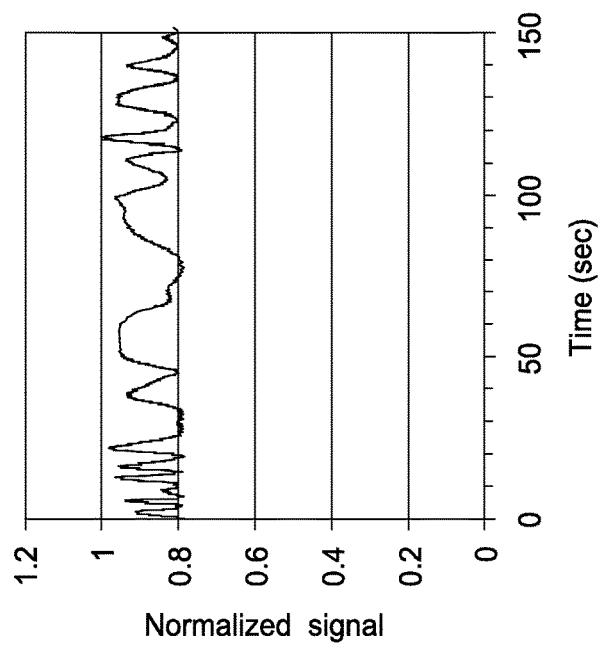
FIG. 3A is a graph showing a transmission signal for a prior art device.
Figure 4B:
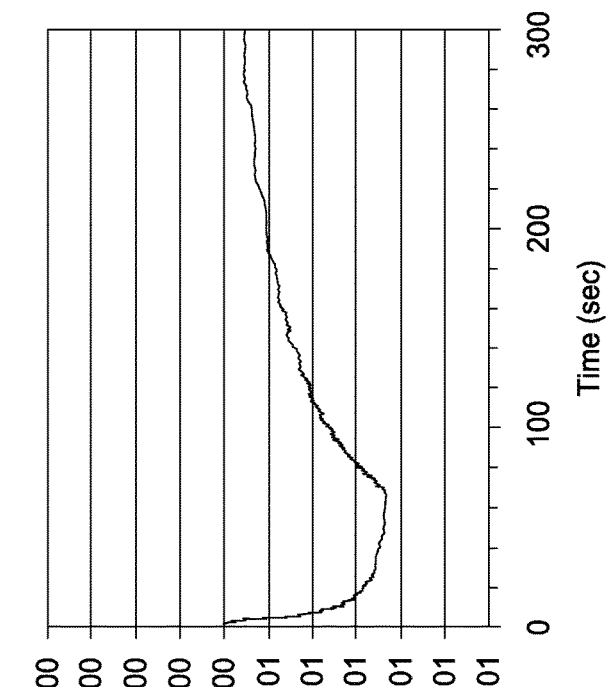
FIG. 4B is a graph showing a transmission signal for a thermal process using a device according to an embodiment of the invention.
Figure 4A:
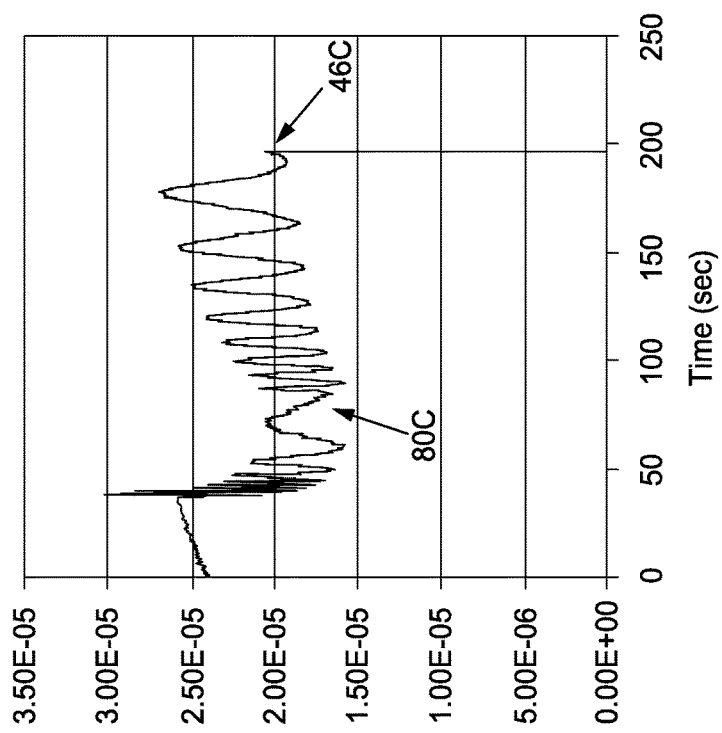
FIG. 4A is a graph showing a transmission signal for a prior art device during a thermal process.

FIG. 3A is a graph showing a transmission signal using a prior art device. Noise is readily apparent in the signal. FIG. 3B is a graph showing a transmission signal using a device as described herein, with substantial reduction of noise. FIG. 4A shows a transmission signal recorded during a thermal process using a prior art device, wherein noise is readily apparent. FIG. 4B is a graph showing a transmission signal during a thermal process using a device as described herein, with substantial reduction of noise.

While the foregoing is directed to embodiments of the present invention, other and further embodiments of the invention may be devised without departing from the basic scope thereof, and the scope thereof is determined by the claims that follow.

The invention claimed is:

1. An apparatus, comprising:
   a substrate support configured to support at least one substrate;
   a source of coherent radiation disposed on a first side of the substrate support, wherein the source is a tunable diode laser;
   a detector for detecting the coherent radiation from the source of coherent radiation, the detector disposed on a second side of the substrate support; and
   a broadband amplifier disposed in an optical path on the first side of the substrate support between the source and the detector and configured to receive the coherent radiation from the source.

2. The apparatus of claim 1, wherein the broadband amplifier is a broadband lasing medium.

3. The apparatus of claim 2, wherein the broadband amplifier includes a fiber Bragg grating.

4. The apparatus of claim 3, wherein the source is a laser that emits radiation at a first wavelength and the fiber Bragg grating emits radiation at a second wavelength and a difference between the first wavelength and the second wavelength is between about 5 nm and about 20 nm.

5. The apparatus of claim 4, wherein the laser is optically coupled to the fiber Bragg grating by an angled coupling.

6. The apparatus of claim 1, wherein the source emits the coherent radiation with a wavelength distribution at a first mode and the broadband amplifier emits radiation with a wavelength distribution at a second mode, and a wavelength difference between the first mode and the second mode is between about 5 nm and about 20 nm.

7. The apparatus of claim 6, wherein the broadband amplifier includes an item selected from the group consisting of a broadband laser, a fiber Bragg grating, a Raman amplifier, a Brillouin amplifier, a fiber laser, and an etalon.

8. The apparatus of claim 1, wherein the source emits radiation with a wavelength distribution at a first mode and the broadband amplifier emits radiation with a wavelength distribution at a second mode, and the first mode is within a gain spectrum of the broadband amplifier.

9. An apparatus, comprising:
   a substrate support configured to support at least one substrate;
   a coherent radiation source disposed on a first side of the substrate support, wherein the coherent radiation source is a tunable fiber coupled laser diode;
   a decorrelator optically coupled to the coherent radiation source along a first optical path thereof, the decorrelator disposed on the first side of the substrate support between the coherent radiation source and the substrate support, wherein the decorrelator is configure to receive coherent radiation from the coherent radiation source, and wherein the decorrelator is a broadband amplifier with a gain spectrum that includes a frequency of the radiation emitted by the coherent radiation source; and
   a detector optically coupled to the decorrelator along a second optical path thereof on a second side of the substrate support and positioned such that radiation leaving the decorrelator passes the substrate support before reaching the detector.

10. The apparatus of claim 9, wherein the coherent radiation source has an emission spectrum with a first primary wavelength, the broadband amplifier has an emission spectrum with a second primary wavelength, and a difference between the first primary wavelength and the second primary wavelength is between about 5 nm and about 20 nm.

11. The apparatus of claim 9, wherein the coherent radiation source is a diode laser with a primary wavelength greater than about 950 nm.

12. The apparatus of claim 9, wherein the coherent radiation source and the decorrelator are coupled together by an anti-reflective optical coupling.

13. The apparatus of claim 9, wherein the decorrelator includes an item selected from the group consisting of a laser, a fiber laser, a Bragg grating, a fiber Bragg grating, a Raman amplifier, a Brillouin amplifier, and an etalon.

14. The apparatus of claim 9, wherein the tunable fiber coupled laser diode and the decorrelator are coupled using an angled polished connection.

15. The apparatus of claim 9, further comprising an optical splitter between the decorrelator and the detector.

16. A method of measuring transmission of radiation through a substrate, comprising:
   emitting, from a coherent radiation source, coherent radiation with a tunable source at a primary wavelength at least partially transmitted through the substrate, the substrate being disposed on a substrate support and the coherent radiation source being disposed on a first side of the substrate support;
   tuning the tunable source;
   broadening, using a decorrelator disposed on the first side of the substrate support, a spectrum of the coherent radiation;
   transmitting the broadened coherent radiation through the substrate; and
   detecting, by a detector disposed on a second side of the substrate support, the radiation transmitted through the substrate, thereby pyrometrically determining a thermal state of the substrate.

17. The method of claim 16, wherein the spectrum is broadened with a decorrelator, and the tuning matches the emitted coherent radiation to properties of the decorrelator.

* * * * *